United States Patent [19]

Merenkova et al.

[11] Patent Number: 6,103,083
[45] Date of Patent: Aug. 15, 2000

[54] CAPILLARY ELECTROPHORESIS APPARATUS AND METHOD

[75] Inventors: Irena N. Merenkova; Maxim Brevnov, both of Moscow, Russian Federation

[73] Assignee: Tetragen, Moscow, Russian Federation

[21] Appl. No.: 09/027,426

[22] Filed: Feb. 20, 1998

[51] Int. Cl.[7] .......................... G01N 27/447; G01N 27/00
[52] U.S. Cl. ........................... 204/603; 204/452; 356/344
[58] Field of Search ......................... 356/344; 250/458.1, 250/461.2, 328; 204/451, 452, 453, 454, 455, 601, 602, 603, 604, 605; 210/657

[56] References Cited

U.S. PATENT DOCUMENTS

| | | |
|---|---|---|
| 3,980,891 | 9/1976 | Slaker . |
| 4,374,723 | 2/1983 | Vesterberg . |
| 4,375,401 | 3/1983 | Catsimpoolas . |
| 4,675,095 | 6/1987 | Kambara et al. . |
| 4,811,218 | 3/1989 | Hunkapiller et al. . |
| 4,832,815 | 5/1989 | Kambara et al. . |
| 4,879,012 | 11/1989 | Kambara et al. . |
| 4,930,893 | 6/1990 | Manian ................................... 356/344 |
| 5,062,294 | 11/1991 | Iwata . |
| 5,091,652 | 2/1992 | Mathies et al. . |
| 5,192,412 | 3/1993 | Kambara et al. . |
| 5,274,240 | 12/1993 | Mathies et al. . |
| 5,324,401 | 6/1994 | Yeung et al. . |
| 5,340,747 | 8/1994 | Eden ................................... 250/461.2 |
| 5,413,686 | 5/1995 | Klein et al. ............................ 204/604 |
| 5,439,578 | 8/1995 | Dovichi et al. ........................ 204/604 |
| 5,483,075 | 1/1996 | Smith et al. . |
| 5,498,324 | 3/1996 | Yeung et al. .......................... 356/344 |
| 5,560,811 | 10/1996 | Briggs et al. .......................... 204/451 |
| 5,597,468 | 1/1997 | Lauer et al. ............................ 204/453 |
| 5,730,850 | 3/1998 | Kambara et al. ...................... 204/452 |
| 5,833,827 | 11/1998 | Anazawa et al. ...................... 204/452 |
| 5,885,430 | 3/1999 | Keman et al. .......................... 204/453 |

FOREIGN PATENT DOCUMENTS

| | | |
|---|---|---|
| 0 314 045 A2 | 10/1988 | European Pat. Off. . |
| 0 497 480 A1 | 1/1992 | European Pat. Off. . |
| 0 533 302 A1 | 3/1993 | European Pat. Off. . |
| 0 723 149 A2 | 1/1996 | European Pat. Off. . |
| WO 94/29712 | 12/1994 | WIPO . |
| WO 96/13716 | 5/1996 | WIPO . |
| WO 96/36872 | 11/1996 | WIPO . |

OTHER PUBLICATIONS

Clark, et al., "High–Speed Parallel Separation of DNA Restriction Fragments Using Capillary Array Electrophoresis[1]", Analytical Biochemistry, 215 :163–170 (1993).

Takahashi, et al., Multiple Sheath–Flow Gel Capillary–Array Electrophoresis for Multicolor Fluorescent DNA Detection, Anal. Chem., 66(7):1021–1026 (1994).

Ueno, et al., "Simultaneous Monitoring of DNA Fragments Separated by Electrophoresis in a Multiplexed Array of 100 Capillaries", Anal. Chem., 66(9):1424–1431 (1994).

Xiaohua C. Huang et al., Capillary Array Electrophoresis Using Laser–Excited Confocal Fluorescence Detection. American Chemical Society 1992, 64, 967–971.

M.A. Quesada, et al., High –Sensitivity DNA Detection With A Laser–Excited Confocal Fluorescence Gel Scanner. BioTechniques, 1991, vol. 10, No. 5, 616–625.

Harold Swerdlow, et al., Three DNA Sequencing Methods of Using Capillary Gel Electrophoresis and Laser–Induced Fluorescence, American Chemical Society, 1991, 63, 2835–2841.

*Primary Examiner*—Robert J. Warden, Sr.
*Assistant Examiner*—Andrew Aldag
*Attorney, Agent, or Firm*—Knobbe Martens Olson & Bear

[57] ABSTRACT

The present invention relates to an electrophoresis apparatus having a plurality of capillaries arranged in a plane such that a curving contour is formed by the intersection points of each of the capillaries with the plane. The apparatus may be used to determine the sequence of nucleic acids. The present invention also relates to methods of using the electrophoresis apparatus and methods of making the electrophoresis apparatus.

59 Claims, 11 Drawing Sheets

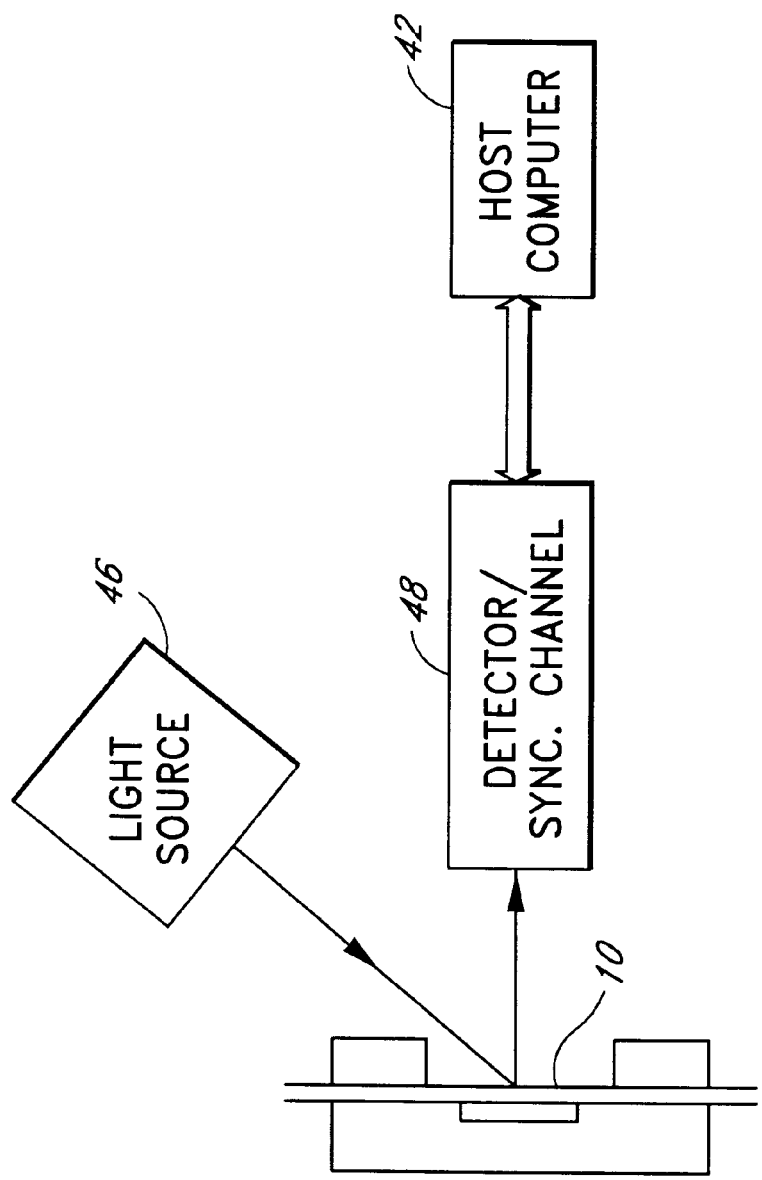
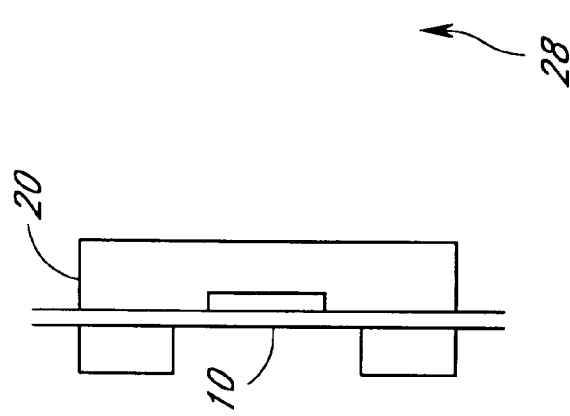
FIG. 4

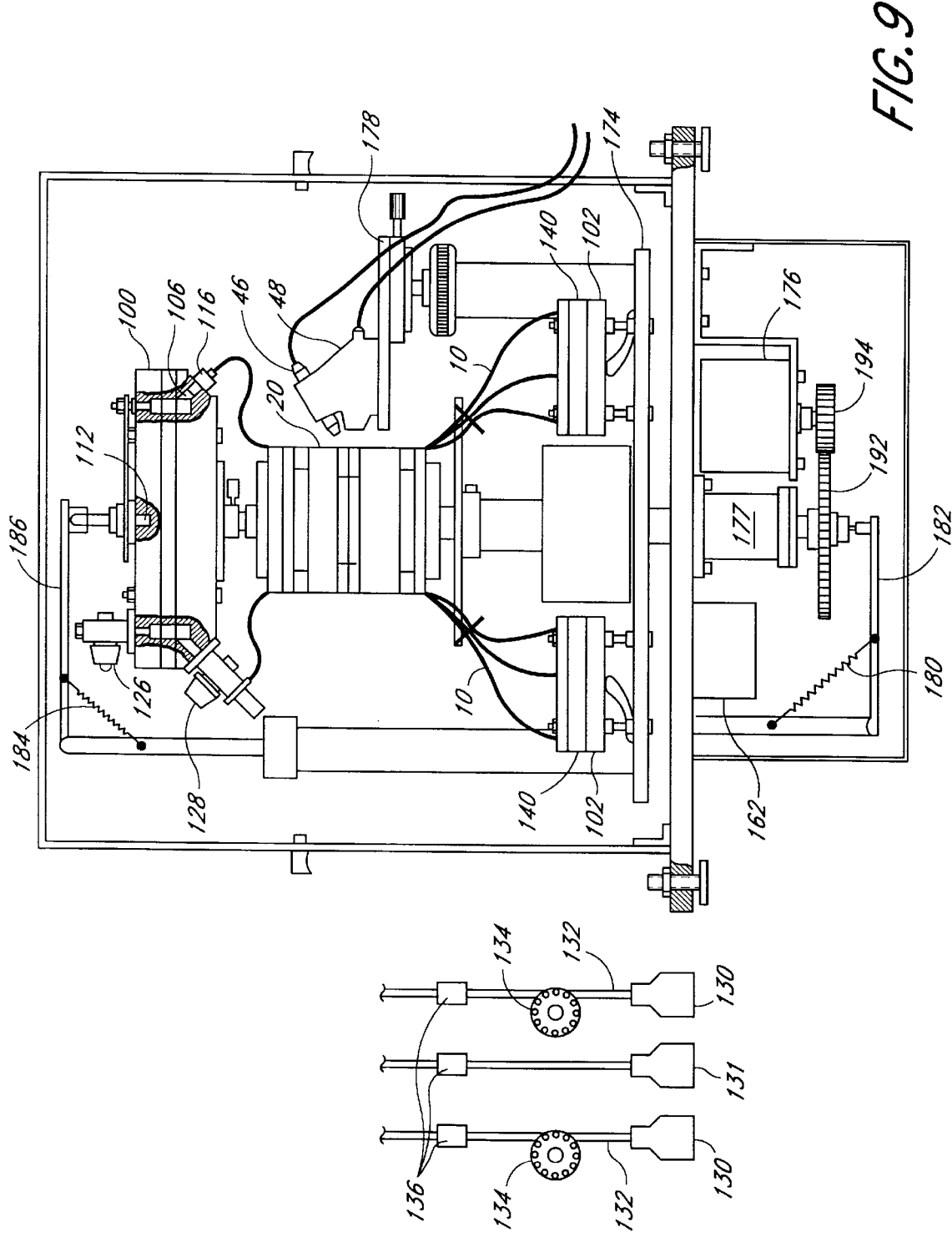

CAPILLARY ELECTROPHORESIS APPARATUS AND METHOD

BACKGROUND OF THE INVENTION

Recent advances in molecular biology have greatly accelerated the rate at which genes can be cloned and characterized, rendering determination of the complete genomic sequence of an organism an attainable goal. Accordingly, large scale genomic sequencing efforts for several organisms including bacteria, yeast, and nematodes have already yielded extensive genomic sequence information. Recently, the Human Genome Project, an ambitious project to obtain the entire sequence of the human genome, has commenced. The Human Genome Project paves the way for an even more ambitious project sometimes referred to as the Human Genome Diversity Project, a project aimed at identifying and characterizing allelic differences between humans which manifest themselves in a phenotypically important manner. For example, some allelic variations may be the source of debilitating diseases such as sickle cell anemia or neoplastic diseases.

With cloning techniques well developed, the rate at which information can be extracted from the cloned DNA becomes a limiting factor in determining the genomic sequence of an organism. Accordingly, advances in automated sequencing will reduce the cost and time required to sequence the genomes of model organisms.

For example, in order to sequence the 3 billion nucleotides in the human genome in a ten year span, it is necessary for the automated sequencing devices to achieve a sequencing rate of three hundred million bases per year. At the same time, the sequence information obtained using these automated systems must be accurate, reliable, and efficient without requiring the involvement of highly skilled personnel to a high degree. In addition, the cost of operating and maintaining the automated sequencing devices must be minimized.

In the past, slab gel electrophoresis was used to sequence DNA. (See U.S. Pat. No. 4,811,218 and EPO 0533302A1, the disclosures of which are incorporated herein by reference). However, such techniques are prohibitively limited in the context of genomic sequencing efforts. Recently, capillary electrophoresis has emerged as a viable approach to genomic sequencing. In capillary electrophoresis the design products of sequencing reactions conducted on the nucleic acids to be sequenced are applied to small diameter capillary tubes containing a separating medium such as a soluble cellulose derivative or polyacrylamide. A high voltage is applied along the tubes, thereby causing the nucleic acids to migrate along the length of the capillary tubes. As in conventional sequencing techniques, the differential migration rates of nucleic acids of different lengths enables sequence determination. Nucleic acids migrating through the capillary tubes are detected upon reaching a detection region in the capillary tubes using such techniques as laser induced fluorescence.

While capillary electrophoresis permits high resolution of nucleic acids of different lengths and rapid sequence determination, several technical hurdles remain in the application of this technology to genomic sequencing efforts. One important limitation in existing methods is the difficulty in obtaining sequence information from a large number of capillaries simultaneously.

Huang et al. provided a device in which multiple capillaries are arrayed side by side as illustrated in FIG. 1, and are sequentially scanned by a laser and fluorescence is detected using a photomultiplier. (See Huang et al., Anal. Chem. 64:967–972 (1992), the disclosure of which is incorporated herein by reference). However, the effectiveness of the device of Huang is reduced as a result of lightscatter from the capillary walls and the interfaces between the separation medium and the capillaries. Furthermore, in the Huang device, the entire stage on which the capillaries are mounted is linearly translated back and forth underneath the light illumination and collection apparatus, resulting in stress on the capillaries and difficulties in precise position control.

Dovichi et al. provided a device in which multiple rows of capillaries terminate at different levels in a sheath flow cuvette. (See WO 94/29712, the disclosure of which is incorporated herein by reference). Sheath fluid draws individual sample streams through the cuvette. However, the device of Dovichi et al. requires a bubble removing system to ensure that bubbles do not form in the cuvette. To reduce background signal the Dovichi device requires the use of highly purified sheath fluid. In addition, in order to achieve the required sensitivity of signal detection, the Dovichi design requires placement of the laser very close to the termini of the capillaries. Finally, with the Dovichi system it is difficult to adjust the system after each use and to change the capillaries.

For the preceding reasons, there is a need for a detection system which achieves a high throughput while requiring little attention by highly trained personnel.

SUMMARY OF THE INVENTION

In one embodiment, the invention comprises an electrophoresis apparatus comprising a plurality of capillaries, wherein each of the plurality of capillaries intersects a plane, and wherein the plurality of capillaries is arranged to intersect the plane such that a curving contour is formed by the intersection points of each of the plurality of capillaries with the plane. Advantageously, such a plurality of capillaries may form a substantially cylindrical array.

Another aspect of the present invention includes an electrophoresis apparatus comprising a plurality of capillaries and a capillary guide. The capillary guide may form a substantially cylindrical shell having an inner surface and an outer surface and may include capillary inputs proximate to a first end and capillary outputs proximate to a second end. The capillaries may then be exposed along a portion of at least one of the inner surface and the outer surface of the capillary guide.

Methods of making electrophoresis apparatus are also provided. In one such embodiment of the invention, a method of making a capillary electrophoresis apparatus comprises the steps of arranging a plurality of capillaries in a substantially cylindrical array and mounting a light collecting lens adjacent to at least one of the plurality of capillaries.

Another aspect of the present invention comprises methods of performing electrophoresis. One such method comprises the steps of rotating an array of capillaries, illuminating capillaries in the rotating array and detecting light emitted by substances in said capillaries. An alternative method of performing electrophoresis comprises the steps of rotating an illuminator past an array of capillaries and detecting light emitted by substances in the capillaries.

Additional electrophoresis apparatus is also provided, including a grid for aligning capillaries with the wells in a microtiter plate. This grid advantageously comprises a body having apertures therein, the apertures being sized for receiving capillaries therein and configured such that the apertures align with the wells in the microtiter plate when the body is placed over the microtiter plate.

BRIEF DESCRIPTION OF THE DRAWINGS

FIG. 4 is a block diagram of a second embodiment of an electrophoresis apparatus in accordance with the present invention.

FIG. 9 is a cutaway view of a stationary optical path embodiment of the electrophoresis apparatus of the present invention.

DETAILED DESCRIPTION OF THE PREFERRED EMBODIMENT

Preferred embodiments of the present invention will now be described with reference to the accompanying Figures, wherein like numerals refer to like elements throughout. The terminology used in the description presented herein is intended to be interpreted in its broadest reasonable manner, even though it is being utilized in conjunction with a detailed description of certain specific preferred embodiments of the present invention. This is further emphasized below with respect to some particular terms used herein. Any terminology intended to be interpreted by the reader in any restricted manner will be overtly and specifically defined as such in this specification.

Figure 2:
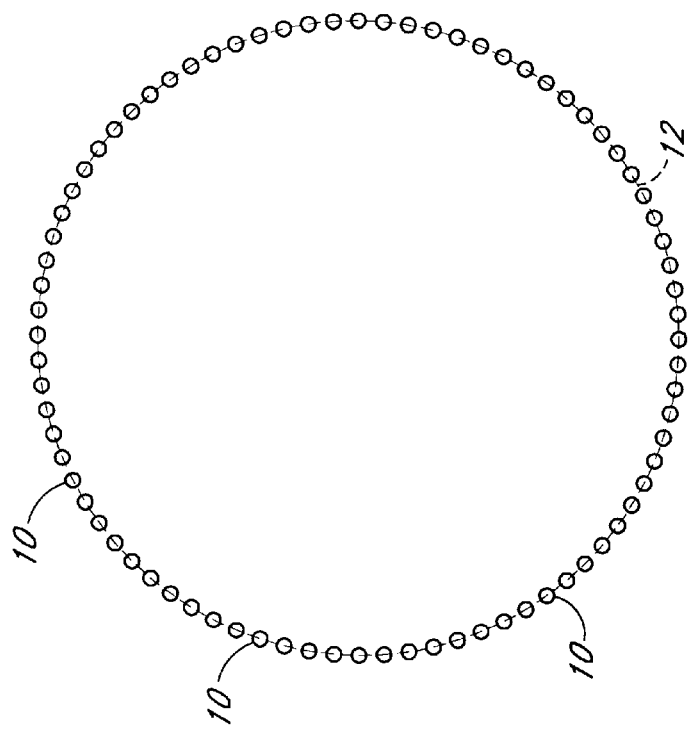
FIG. 2 is a cutaway end view of a cylindrical array of capillaries according to the present invention.
Figure 1:
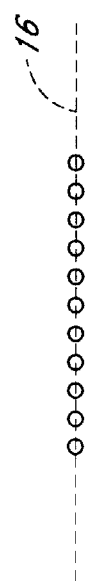
FIG. 1 is a cutaway end view of an open linear array of capillaries as provided by some prior art devices.

In one aspect of the present invention, an electrophoresis apparatus includes a novel arrangement of a plurality of capillaries. To illustrate, FIG. 2 shows a cutaway end view of a capillary arrangement according to one aspect of the present invention. As shown in this Figure, each of the capillaries 10 intersects a plane which in FIG. 2 would be transverse to the direction of capillary extension and parallel with the plane of the paper on which FIG. 2 is drawn. When the intersection points are connected, they form a curved contour 12 in the plane of intersection. In advantageous embodiments described in more detail below, the curved contour is substantially closed. In contrast, prior art multi-capillary electrophoresis machines, as shown in FIG. 1, only open linear contours 16 are created by linking their respective intersection points with a similarly defined plane. In one advantageous embodiment, the substantially closed contour which is formed is substantially circular. This specific arrangement is illustrated in FIG. 2. As will be explained below, a capillary arrangement which forms such a closed contour provides significant advantages over the linear arrangement of the prior art. Specifically, it is one advantage of such a configuration that various forms of rotating apparatus can be devised which allow improvements in speed and simplicity for high throughput electrophoresis screening. Two of these rotating configurations are described below with reference to FIGS. 3 and 4. In the FIG. 3 embodiment, an optical path for illumination and light collection rotates inside a capillary array. In the FIG. 4 embodiment, a capillary array rotates past a stationary optical path for illumination and light collection.

Figure 3:
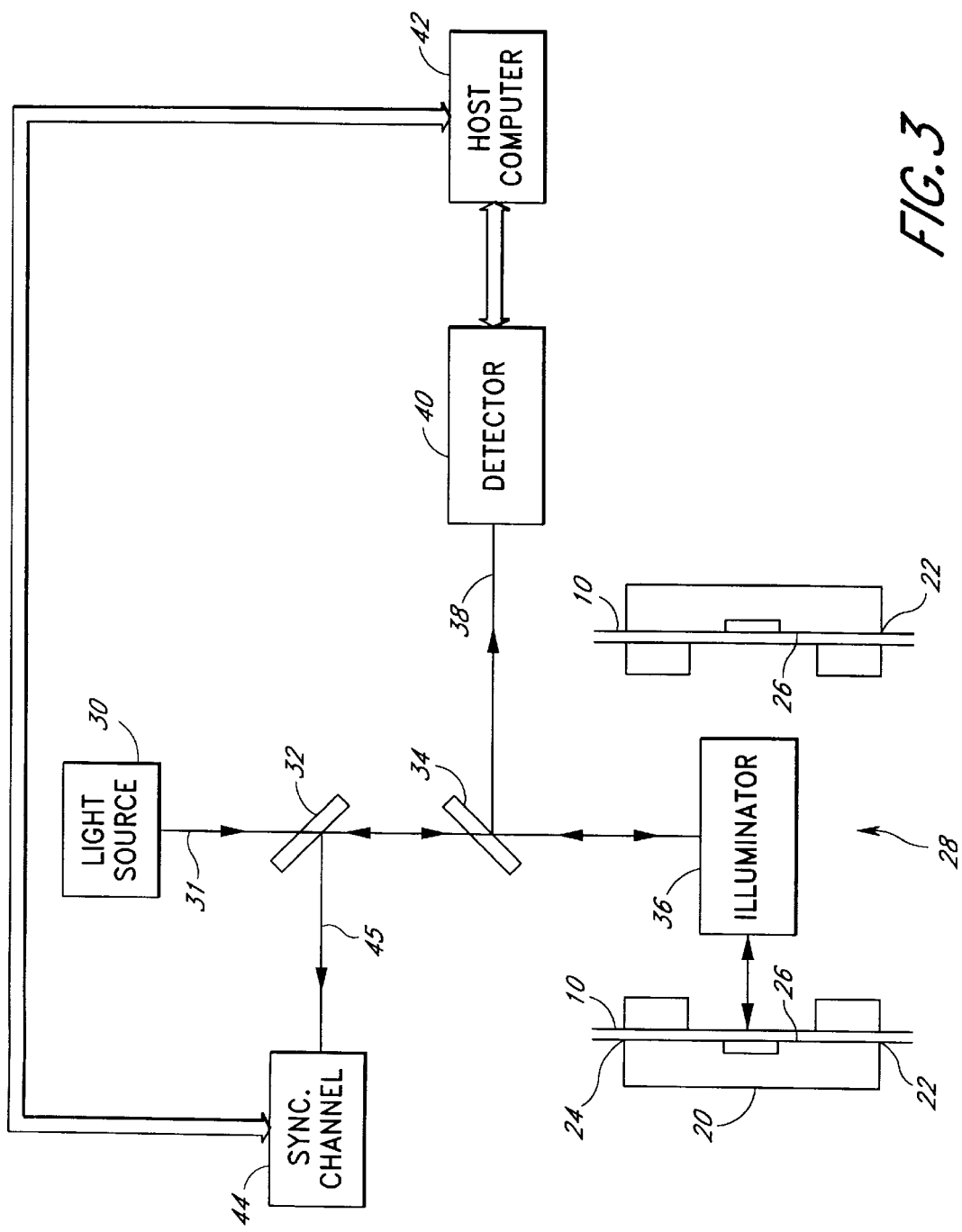
FIG. 3 is a block diagram of a first embodiment of an electrophoresis apparatus in accordance with the present invention.

Referring now to FIG. 3, a first electrophoresis apparatus is illustrated which incorporates the capillary arrangement illustrated in FIG. 2. The illustrated electrophoresis apparatus includes a light source 30, which may advantageously comprise an approximately 50 milliwatt argon-ion laser commonly used for exciting fluorescence in various biological spectroscopy applications. The light source 30 transmits light 31 through first and second partially reflective mirrors designated 32 and 34 respectively. After passing through the mirrors 32, 34, the laser light is routed to an illuminator 36 which is positioned inside a substantially cylindrical capillary guide 20 (illustrated in cross section in FIG. 3) which supports a plurality of capillaries 10 in the arrangement of FIG. 2. In this embodiment, therefore, the illuminator 36 does not generate light, but only directs it to the capillaries 10. This is a preferred configuration, although a system having a light source 30 integral with the illuminator 36 may also be utilized.

Each capillary 10 extends into the guide 20 via a lower capillary input 22 on one end. Each capillary 10 exits the guide 20 through a capillary output 24 on the other end. In the FIG. 3 embodiment, the inputs 22 and outputs 24 comprise holes drilled through upper and lower portions of the guide 20. Along an inner surface 26 of the guide 20 the capillaries are exposed to the open inside region 28 of the guide 20. The capillaries may be held in place in grooves or indentations on the inner surface 26 of the guide with or without optical glue or other mechanical securement. Of course, the capillaries are connected on respective ends to buffer and sample material, as well as an electric potential for causing species migration through internal polymer. These aspects of some embodiments of the present invention are described in more detail below with reference to FIGS. 9–18.

The illuminator 36 directs the laser light 31 to the exposed portion of the capillaries on the inside of the guide 20. As will be explained in more detail below with reference to FIG. 5, in some advantageous embodiments the illuminator rotates inside the guide 20, so that each capillary 10 in the cylindrical array is sequentially exposed to the laser light 31. The illuminator further collects light emitted from substances within the capillary, from laser excited fluorescence, for example, with the same lens system used to route the laser light 31. A portion of this emitted light 38 is transmitted to a detector 40 by one of the partially reflective mirrors 34. The detector outputs data to a host computer system 42 to produce emission profiles for each capillary 10 in the array as a function of time. In some advantageous embodiments, the illuminator may rotate once around the array every 0.5 to 2 seconds, preferably approximately once per second, which will produce about 5 to 20 emission data points for a typical fluorescence band during, for example, DNA sequencing.

As is also seen in FIG. 3, the electrophoresis apparatus of the present invention may further comprise a synchronization detector 44. This detector may, for example, be a photodiode configured to be sensitive to light at the excitation frequency of the laser 30 which has been scattered by capillary surfaces and interfaces. The intensity of this scattered light will peak when the beam is centered directly over a capillary wall, and be minimal when the beam is between capillaries. This signal can be used to ensure the synchronization of data sampling and capillary illumination, and minimizes the amount of optics/capillary alignment which must be performed to collect data from hundreds or thousands of capillaries. In some embodiments, it is advantageous to include a larger space between the first capillary of an array and the last capillary of an array. The longer than usual period between signals from the synchronization detector thus produced can be detected and used to recognize the first capillary of the array. It will be appreciated by those of skill in the art that appropriate band-pass and/or band-stop filters may be used in the synchronization beam 45 and the collected emitted light beam 38.

An additional embodiment having a stationary optical path and a rotating capillary guide 20 is illustrated in FIG. 4. In this embodiment, the inside region 28 of the guide 20 contains no illuminator, and the capillaries 10 are secured to the outer surface of the guide 20 rather than the inner surface. A light source 46, of a nature similar to that described above with regard to FIG. 3, is provided outside the guide 20 so as to illuminate the capillaries 10 on the outer surface of the guide. In addition, a detector 48, coupled to a host computer 42 are also provided outside the guide 20. In this, embodiment, as will also be described below with reference to FIG. 7, the synchronization channel is provided as part of the detector assembly 48. In the embodiment of FIG. 4, the guide 20 and attached capillary array rotate, while the light source and collection apparatus remain stationary. In this embodiment, the capillary array may rotate approximately 0.5 to 2 times per second, preferably approximately 1 revolution per second. Although the configuration of FIG. 4 requires moving capillaries which are not required in the FIG. 3 embodiment, the light path remains stationary, thereby simplifying the optics of the system. In particular, accurate focusing of the light beam is easier with this embodiment, because no precise alignment of the beam with the central portion of a rotating mirror is needed.

The advantages to the curved contour capillary array configuration over the linear array may now be appreciated, and can be seen to increase substantially with increases in the number of capillaries in a given array. Because the rotation rate will remain constant regardless of the number of capillaries in the array, the mechanical problems associated with scanning truly large numbers of capillaries are greatly reduced. Furthermore, the fact that the array of capillaries defines a closed contour (as described above with reference to FIG. 2) allows the scanner to be adjacent to the first capillary immediately following a scan of the last capillary. This is not possible with the open contour linear array, where a return to the opposite side of the array must be made after each pass. This results in an overall decrease in the average relative speed over a given distance between the capillaries and the light beam optics of about 50% as compared to the open contour linear capillary array.

For example, with one millimeter between the center of each capillary 10, a 1000 capillary electrophoresis device according to the present invention as illustrated in FIG. 4 may include an approximately 1 Hz rotating capillary guide which is approximately 37 cm diameter cylindrical capillary array. For a similar linear array, the array width would be one meter, and the linear speed of the beam optics relative to the capillaries would need to average at least 2 meters per second. This linear scanning motion would further include large accelerations as it changed direction at either end of the array. As the number of desired capillaries increases above this example 1000 capillary array, the relative ease of upward scaling of the cylindrical array relative to the linear array becomes even more pronounced.

Figure 5:
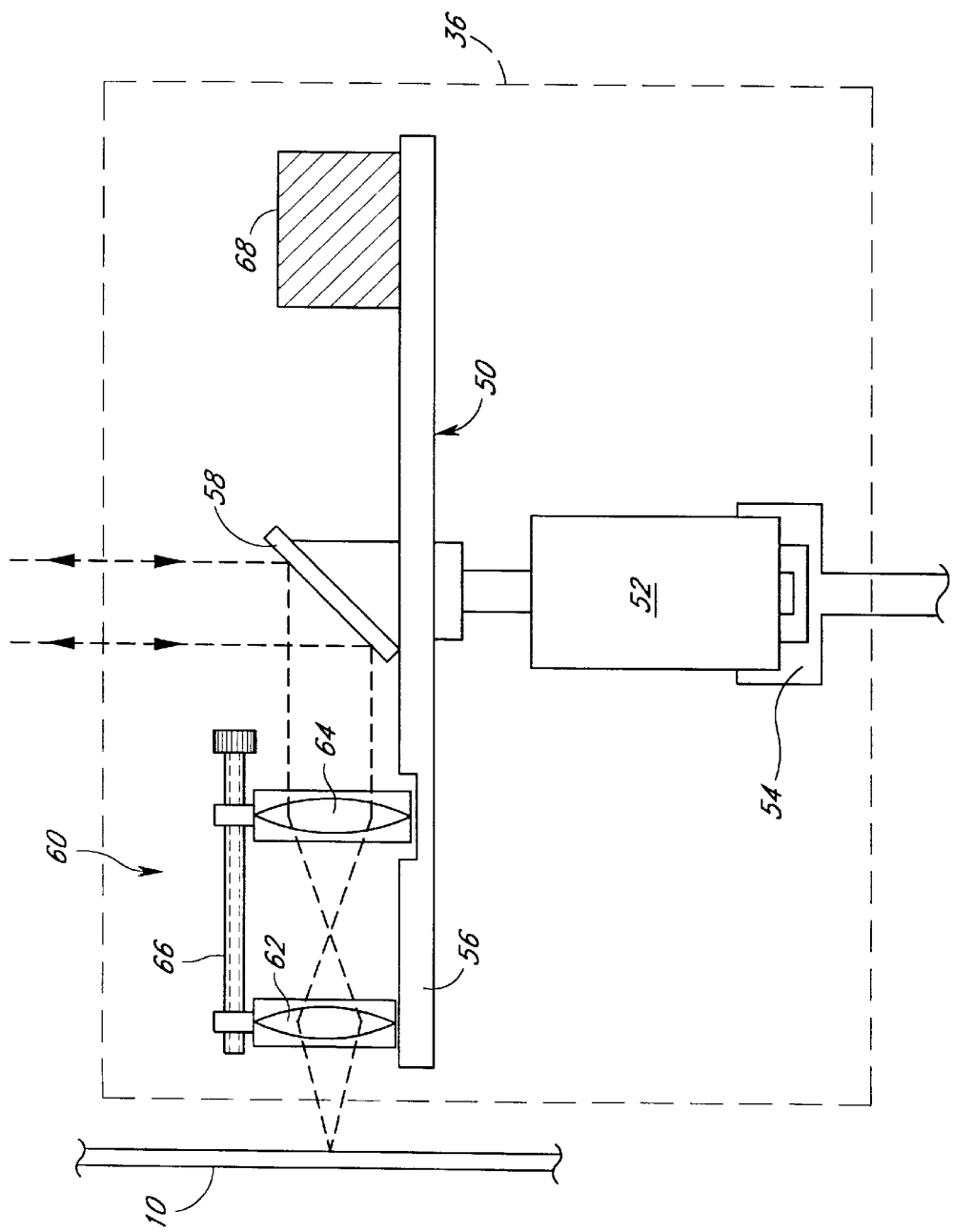
FIG. 5 is a detailed view of the illuminator of FIG. 3.

Referring now to FIG. 5, a detailed illustration of one advantageous embodiment of the illuminator 36 of FIG. 3 is provided. The illuminator 36 may comprise a platform 50 mounted on the shaft of a motor 52 which is held inside the capillary guide 20 by a support arm 54 which extends out one end of the capillary guide 20. The platform has a length so that at least one end 56 extends almost to the inner surface 26 of the capillary guide 20. The platform 50 provides a mounting surface for a centrally located mirror 58 which is angled at approximately 45 degrees from the horizontal.

At one end 56 of the platform 50 is a conventional compound microscope 60 which may take any one of many forms known in the art. In FIG. 5, the microscope is illustrated as comprising an objective lens 62, an eyepiece 64, and a focus adjustment screw 66. The microscope 60 focuses the laser light onto a region inside an adjacent capillary 10, and also collects light emitted by substances within the capillary 10 in a manner well known in the art. The platform may further have mounted thereon a counterweight 68, which can be adjusted in weight and position to provide rotational stability to the platform 50.

Figure 6:
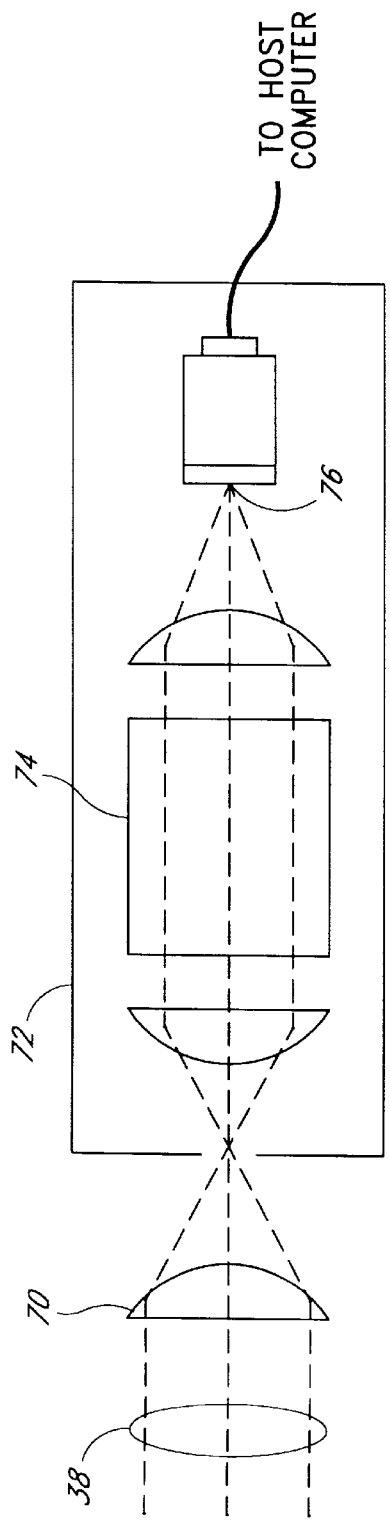
FIG. 6 is a detailed view of the detector of FIG. 3.

FIG. 6 is a more detailed illustration of the detector 40 of FIG. 3. The detector comprises a lens 70 which focuses the emitted light beam 38 through a small opening in a substantially light tight enclosure 72. Inside the enclosure is a spectral separator 74, which transmits light of different wavelengths emitted by the illuminated region of the capillary onto different locations on a linear, single line charge coupled device (CCD) 76. Spectral separators including prisms or diffraction gratings which are suitable for use with the present invention are well known to those of ordinary skill in the art. Thus, for DNA sequencing using a different fluorescent dye for each base, the CCD can be broken up into regions corresponding to the approximate emission wavelength of each dye.

Figure 7:
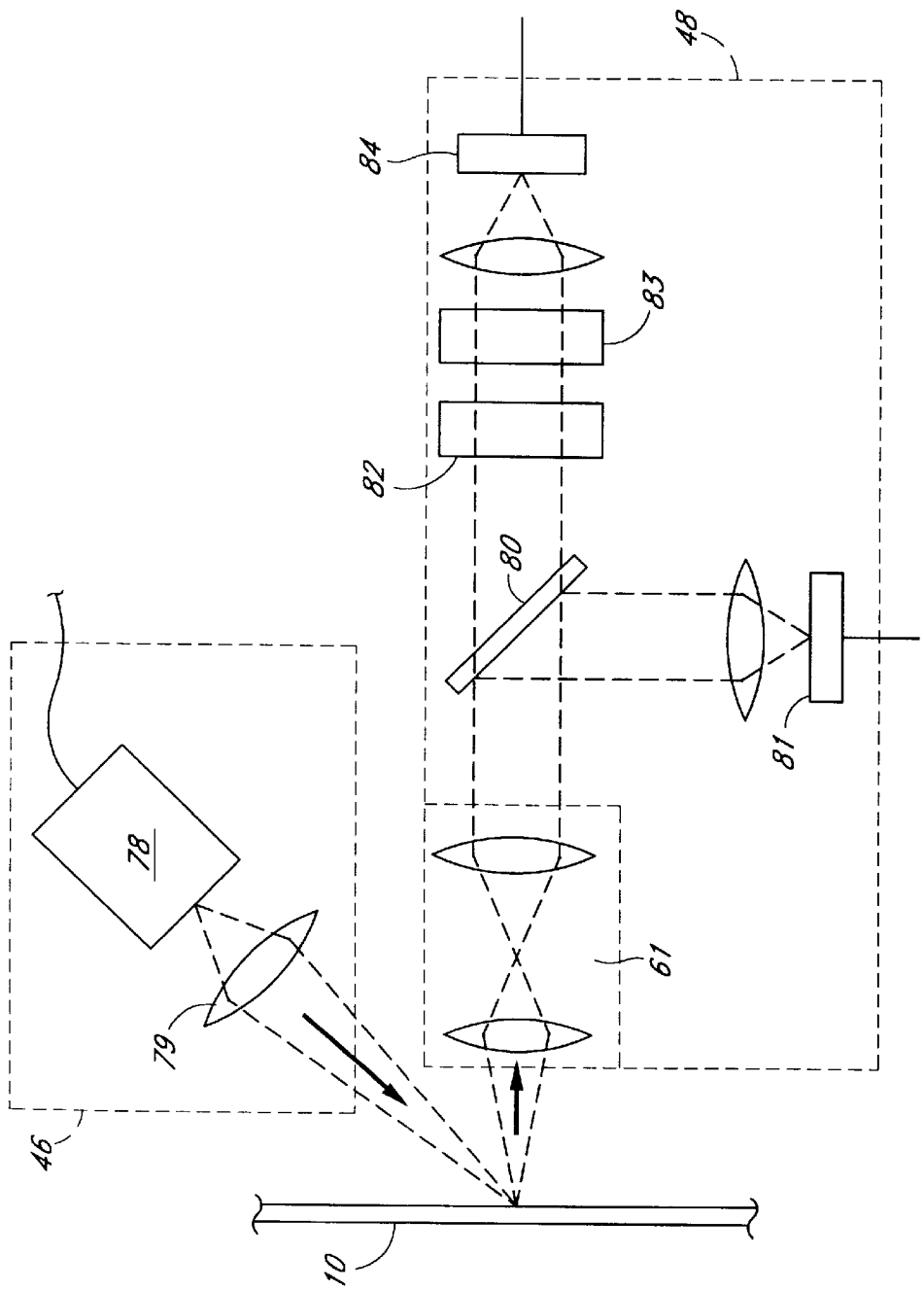
FIG. 7 is a detailed view of the detector/synchronization channel of FIG. 4.

It can be appreciated that the configuration of the apparatus for illuminating and detecting fluorescence is somewhat different for the rotating capillary array of FIG. 4. One advantageous embodiment of this apparatus is illustrated in FIG. 7. As shown in FIG. 7, the light source 46 comprises a source of laser light 78 analogous to that described above. In this embodiment, the laser light may advantageously be routed to the capillary array through an optical fiber. The light source 46 also comprises an appropriate focusing objective lens 79. The detector/synchronization channel 48 includes a microscope 61 analogous to the microscope 60 of the illuminator 36 of FIGS. 3 and 5. The angle between the illuminating light beam and the axis of the light collecting objective is advantageously approximately 45 degrees.

The synchronization channel is created by a partially reflective mirror 80 (an unsilvered glass plate has been found suitable) which directs a small amount of the collected light to a photodiode 81, and operates in a manner analogous to that described above with reference to FIG. 3. The detector 48 additionally includes a rejection filter 82 after the mirror 80 for filtering out light at the fluorescence excitation frequency. A spectral separator 83 and CCD array 84 as described above with reference to FIG. 6 are further provided.

Figure 8:
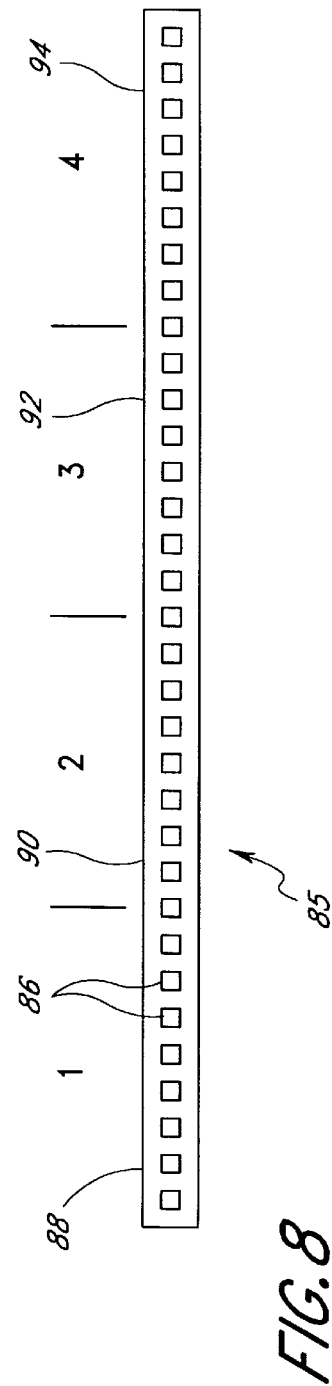
FIG. 8 is an front view of the single line charge coupled device of FIG. 6 and FIG. 7.

A more detailed view of the single line charge coupled device 85 is provided in FIG. 8. As shown in this Figure, the device 85 comprises a linear array of pixels 86. Captured charges which result from incident photons on each pixel are periodically read out. It will be appreciated that the pixels of FIG. 8 are representative only, and that their number and size may vary. This array is positioned relative to the spectral separator 74, 83 (FIGS. 6 and 7) such that light from different fluorescent dyes will illuminate different portions of the linear CCD array. In a four dye DNA sequencing scheme, for example, the array can be segmented into four adjacent regions 88, 90, 92, 94, each chosen to span the peak emission wavelength of one of the four dyes being used. With this system a single CCD array can be used to distinguish multiple dye emissions of different wavelengths without the use of filters.

In prior art capillary electrophoresis apparatus, the typical light detector has been a photomultiplier tube. One reason these devices have been preferred over CCD detectors is that the output is a real-time continuous readout of incident light intensity. In contrast, a CCD element must collect charge for a given period of time under illumination, and this must be followed by a pixel read operation, during which time the collected charge is read out, but the incident light intensity is not being measured. The time taken for this data read operation may limit the rate at which capillaries can be scanned by any one individual CCD pixel. In some embodiments of the present invention, the readout is performed when the illuminating beam is between capillaries. It has been found suitable to leave a space between capillaries of approximately one capillary in width for the read operation. Because the time between capillary illuminations is used for reading out the intensity data, impact on scanning speed is reduced.

The host computer 42 receives this intensity data from the CCD array and interprets the detected light to deliver information to the user regarding the substances which are passed through the capillaries. In one specific example, DNA may be sequenced with a four spectral channel method, where each terminating base is coupled to a dye which fluoresces at a different wavelength. This technique is also described in more detail below, and is currently performed in various electrophoresis protocols. In this example, the host computer 42 may create four separate data files for each capillary. Each file comprises a series of intensity measurements made at approximately one second intervals, with each measurement being a weighted sum of the measured intensities for pixels in a respective one of the four segments of the array. These data sets can be processed in a variety of ways. Spectral cross talk can be eliminated by correlating measurements from adjacent capillaries, and time or frequency domain low pass filtering may be performed. Mobility shift compensation can also be performed prior to peak detection and base identification. Preferably, this process results in a printed 4-letter format base sequence for the DNA sample tested through a given capillary.

Figure 10:
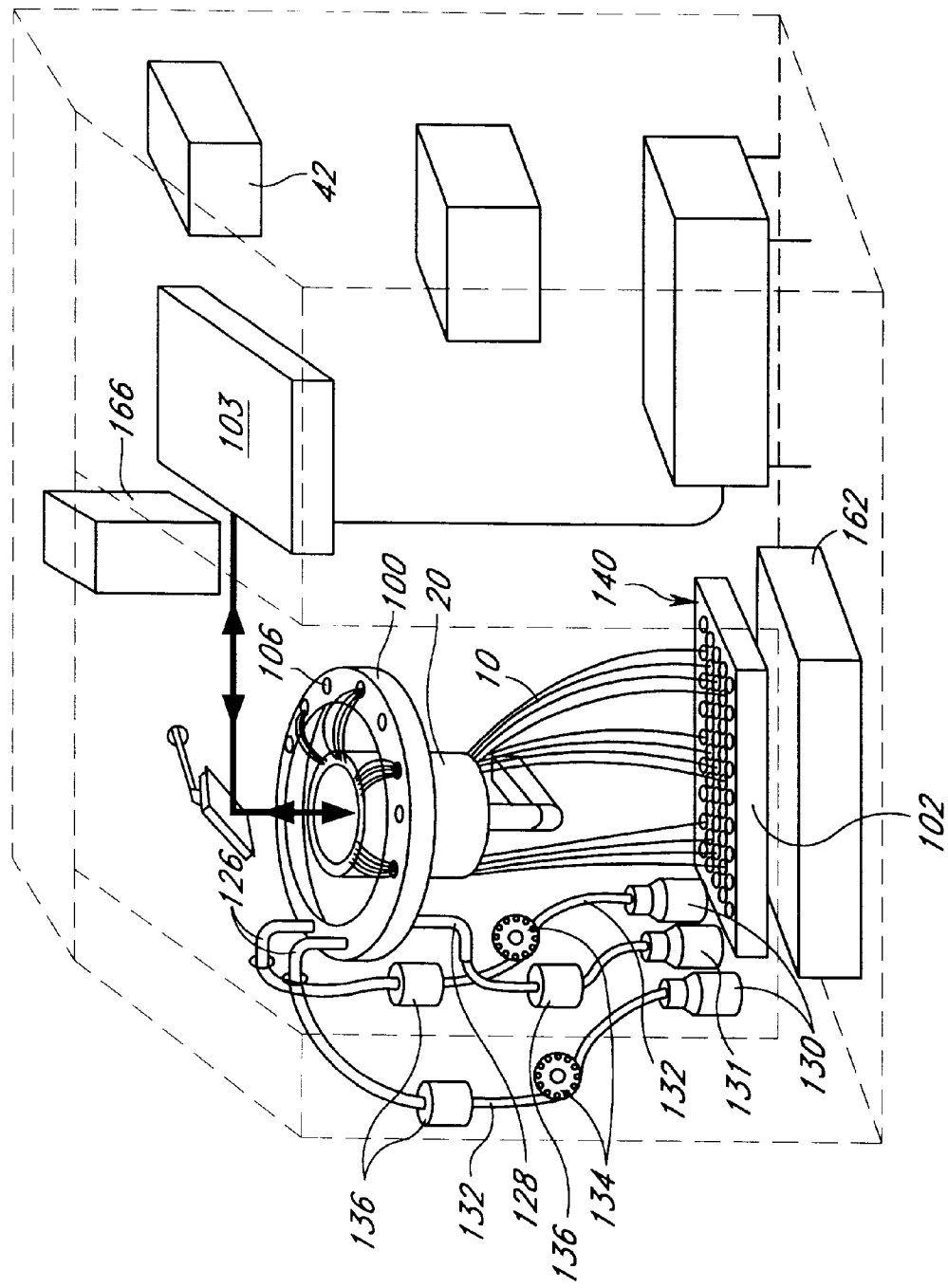
FIG. 10 is a cutaway view of a rotating optical path embodiment of the electrophoresis apparatus of the present invention.

In addition to the detection system described above, the electrophoresis apparatus comprises an electrophoresis portion illustrated in detail in FIGS. 9 and 10. This electrophoresis portion comprises an upper buffer chamber, a lower buffer chamber, a plurality of capillaries extending between the upper buffer chamber and the lower buffer chamber, and a voltage source 162 connected to the upper buffer chamber and the lower buffer chamber. In some embodiments, the electrophoresis portion may further comprise a capillary guide which supports the portions of the capillaries disposed between the upper buffer chamber and the lower buffer chamber. In addition, in some embodiments, the electrophoresis portion of the electrophoresis apparatus may further comprise a filling/refilling system for filling and refilling the capillaries and upper buffer chamber with buffer/separation medium without detaching the capillaries from the device. In some embodiments, the electrophoresis portion is thermoisolated from the remainder of the system such that the temperature at which electrophoresis is performed can be regulated and maintained.

Two embodiments of the present invention are illustrated in FIGS. 9 and 10. However, it will be appreciated that the physical arrangement of the components of the present electrophoresis system may be varied from those shown in FIGS. 9 and 10 without affecting the operation of the device. Accordingly, those of skill in the art will appreciate that such variations fall within the scope of the present invention.

As discussed above in conjunction with FIG. 4, the present invention includes an embodiment wherein the optical path remains stationary while the capillary guide rotates. On such embodiment, illustrated in FIG. 9, will be referred to herein as the "stationary optical path embodiment." In another embodiment, discussed above with reference to FIG. 3, the optical path rotates while the capillary guide remains stationary. One such embodiment, illustrated in FIG. 10, will be referred to herein as the "rotating optical path embodiment." In FIG. 10, the illuminator is inside the capillary guide 20, and is accordingly not shown in this Figure.

As shown in FIGS. 9 and 10, the upper buffer chamber 100 is disposed above one or more lower buffer chambers 102. A plurality of capillaries 10 are disposed between the upper buffer chamber 100 and the lower buffer chambers 102. As shown in FIGS. 9 and 10, a capillary guide 20 may be disposed between the upper buffer chamber 100 and the lower buffer chamber 102. The capillary guide 20 provides support for the portions of the capillaries 10 disposed between the upper buffer chamber 100 and the lower buffer chambers 102. In addition, the capillary guide 20 fixes the capillaries 10 in a closed contour configuration as described above.

Preferably, the capillary guide 20 is a cylindrical tube with a circumference smaller than the circumference of the upper buffer chamber 100. The capillaries 10 are secured to the capillary guide by optical glue, spring rings, or other securing devices known to those skilled in the art.

In the rotating optical path embodiment of FIG. 10, a portion of each of the capillaries 10 passes through the interior of the capillary guide 20 as illustrated in cross section in FIG. 3. In the stationary optical path embodiment, at least a portion of each of the capillaries is disposed on the exterior of the capillary guide 20.

In the stationary optical path embodiment of FIG. 9, the upper buffer chamber 100, capillary guide 20, capillaries 10, and lower buffer chambers 102 are mounted on a platform 174. The platform 174 is driven by a motor 176 which is coupled to a drive shaft/gear box 177. When the motor 176 is activated, the platform 174 rotates. As discussed above, the motor may rotate the platform at a rate of about 0.5 to 2 revolutions per minute. Preferably, the motor rotates the platform at a rate of about 1 revolution per minute.

As the platform 174 rotates, the capillaries 10 on the exterior of the capillary guide 20 sequentially pass in front of the illuminator 46 which is mounted on a fixed platform 178. As each capillary passes before the illuminator 46, the capillary is exposed to the laser light, and the light emitted from the sample passing through the illuminated portion of the capillary is detected.

In the rotating optical path embodiment of FIG. 10, the light source 30, synchronization channel 44, and detector 40 of FIG. 3 are all provided inside a single light tight enclosure 103. In this embodiment, the capillary guide 20 is fixed in place and the illuminator 36 rotates inside the central cavity of the capillary guide. The capillaries 10 are sequentially exposed to laser light by the rotating illuminator 36 positioned inside the central cavity of the capillary guide 20.

As illustrated in FIGS. 9 and 10, an electrical power source 162 is electrically connected to the upper buffer chamber 100 and the lower buffer chambers 102. Those skilled in the art will appreciate that the upper buffer chamber 100 and the lower buffer chamber 102 can be electrically connected to the power source 162 in a variety of ways. For example, in the stationary optical path embodiment of FIG. 9, the electrical power source 162 may be electrically connected to the lower buffer chambers 102 via contacts 180 and 182 beneath the rotating platform 174. One end of contact 182 may be electrically connected to conductors inside the lower buffer chambers 102.

In the rotating optical path embodiment of FIG. 10, the lower buffer chambers 102 may be directly connected to the electrical power source 162.

Figure 11:
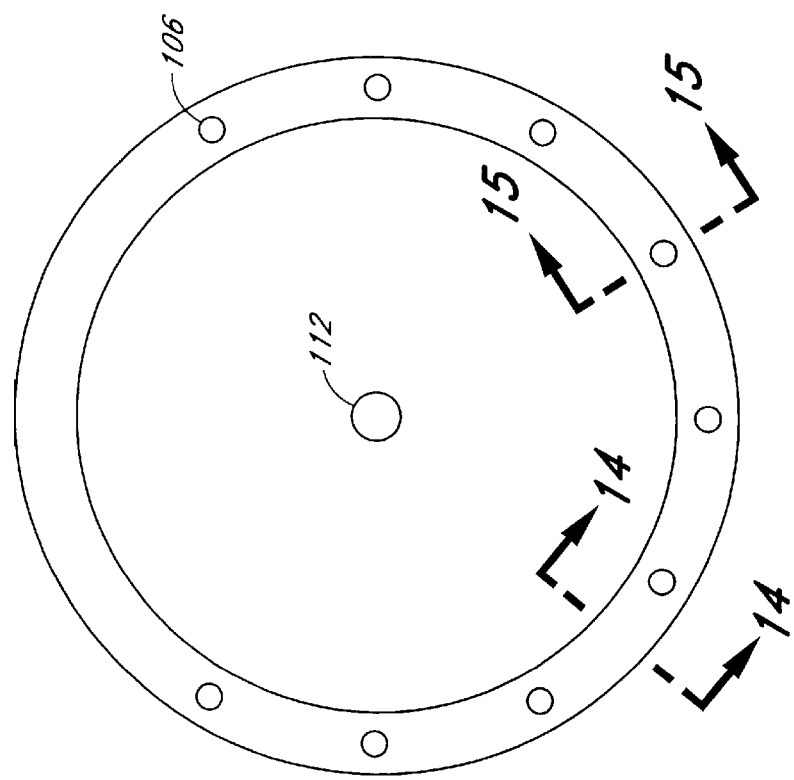
FIG. 11 depicts the bottom of the upper buffer chamber of the stationary optical path embodiment of FIG. 9.
Figure 13:
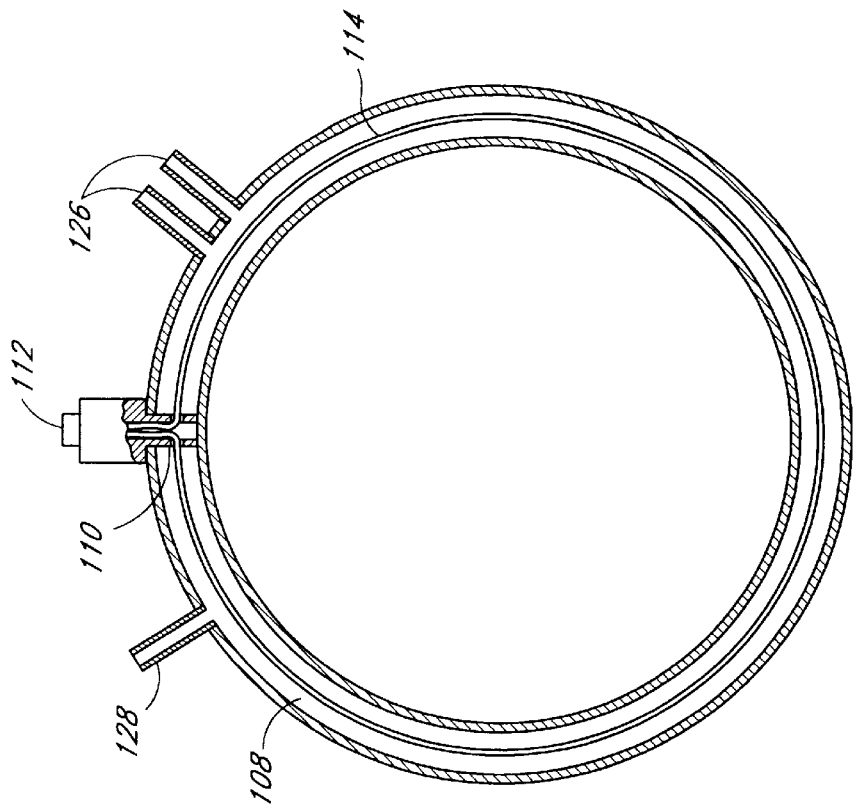
FIG. 13 is a cross section of the upper buffer chamber of FIG. 12.
Figure 12:
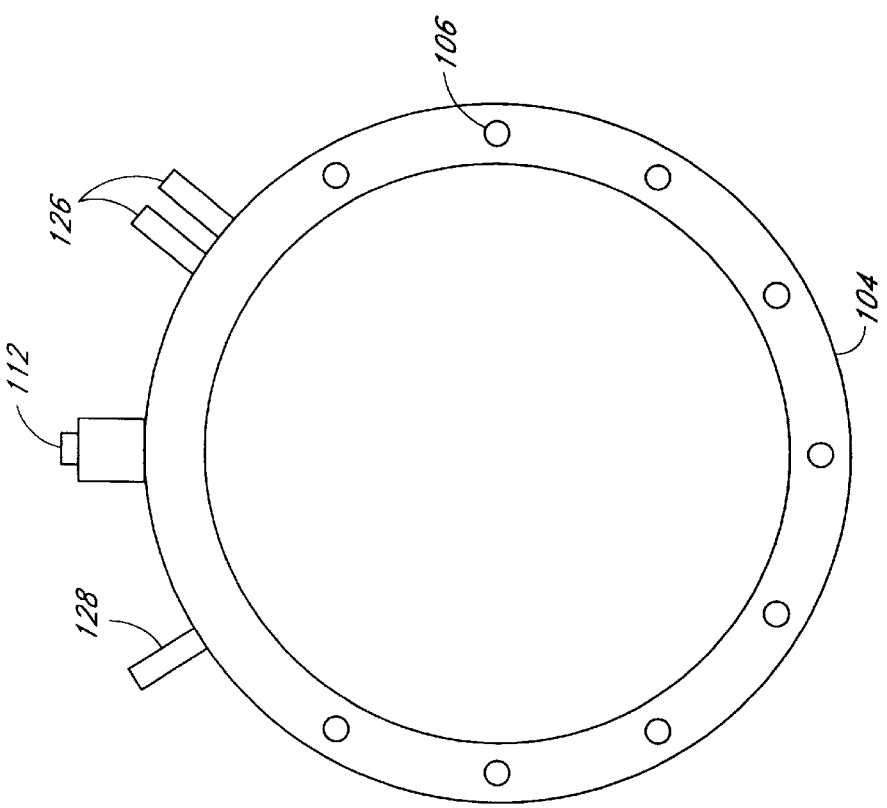
FIG. 12 is a top view of the upper buffer chamber of the rotating optical path embodiment of FIG. 10.

The structure of the upper buffer chamber 100 is shown in more detail in FIGS. 11, 12, and 13. The upper buffer chamber 100 comprises a housing 104 having one or more apertures 106 therein for receiving the upper portions of the capillaries 10.

FIG. 11 depicts the bottom of the upper buffer chamber 100 of the stationary optical path embodiment of FIG. 9. As illustrated in FIG. 11, in this embodiment, the apertures 106 may be located on the lower surface of the upper buffer chamber 100. A spindle 112 runs through the center of the upper buffer chamber 100 to electrically connect the upper buffer chamber 100 to a voltage source 162 through contacts 184 and 186. The spindle 112 is mechanically connected to the motor 176 through gears 192 and 194.

FIG. 12 is a top view of the upper buffer chamber of the rotating optical path embodiment of FIG. 10. FIG. 13 is a cross section of the upper buffer chamber of FIG. 12. As illustrated in FIGS. 12 and 13, in the rotating optical path embodiment of FIG. 10, the apertures 106 may be located on the upper surface of the upper buffer chamber 100.

The upper buffer chamber 100 may have a variety of configurations which array the capillaries 10 in a substantially closed contour. Preferably, the upper buffer chamber 100 is annular in shape. In some embodiments, the interior of the apertures 106 may be threaded to receive an adaptor for securing the capillaries 10 to the upper buffer chamber 100 as described below.

Figure 15:
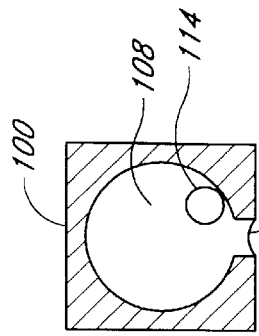
FIG. 15 is a cross section of the upper buffer chamber of FIG. 11 taken along line 15—15.
Figure 14:
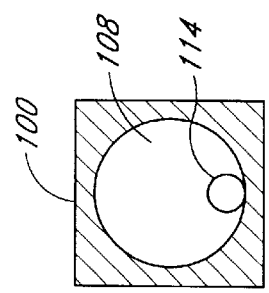
FIG. 14 is a cross section of the upper buffer chamber of FIG. 11 taken along line 14—14.

As shown in FIGS. 13, 14, and 15 the interior of the upper buffer chamber 100 has a channel 108 therethrough for receiving the electrophoresis buffer/separation medium. The channel 108 runs throughout the circumference of the upper buffer chamber 100 but may be interrupted by a partition 110 (illustrated in FIG. 13) in those embodiments equipped with a filling/refilling system as described below, The partition 110 permits the flow of electrophoresis buffer/separation medium to be directed along a desired path during filling or refilling. As shown in the cross section of FIG. 15, the channel 108 in the upper buffer chamber is in fluid communication with the apertures 106 therein.

A connector 112 for connecting the upper buffer chamber 100 to a voltage source 162 is located on the exterior of the upper buffer chamber 100. In the stationary optical path embodiment, the connector 112 may be a spindle which extends from the motor through the upper buffer chamber 100 as illustrated in FIG. 11. In the rotating optical path embodiment, the connector 112 may be on the side of the upper buffer chamber 100 as illustrated in FIGS. 12 and 13.

As illustrated in FIGS. 13, 14, and 15 an electrical conductor 114 is positioned on the lower surface of the channel 108 and runs along the entire circumference of the upper chamber 100. As shown in FIG. 13, in some embodiments having a partition 110 in the channel 108, such as the rotating optical path embodiment of FIG. 10, the electrical conductor 114 passes through the partition 110 and is secured to the connector 112, thereby allowing the potential difference from the voltage source 162 attached to the connector to be applied across the buffer in the upper chamber 100. Alternatively, in some embodiments having a partition 110 in the channel 108, such as the stationary optical path embodiment of FIG. 9, the potential difference from the voltage source 162 may be applied through the spindle 112. In those embodiments which lack the partition 110, the electrical conductor is secured to the connector or spindle 112 on the interior surface of the upper buffer chamber 100.

As shown in FIGS. 9 and 10, bundles of capillaries 10 pass through the apertures 106 in the upper buffer chamber 100. The capillaries 10 may be any of the capillaries conventionally used for capillary electrophoresis, such as the fused silica capillary tubes available from Polymicro, Phoenix, Ariz. having inner diameters of 50 $\mu$m or 100 $\mu$m. The number of bundles of capillaries 10 entering the upper buffer chamber 100 may vary depending on the number of samples which are to be evaluated in each run. Preferably, there are a plurality of bundles of capillaries 10 attached to the upper buffer chamber 100. The number of capillaries 10 in each bundle may vary depending on the number of samples which are to be evaluated in each run. Preferably, there are at least 50 capillaries in each bundle.

Figure 16:
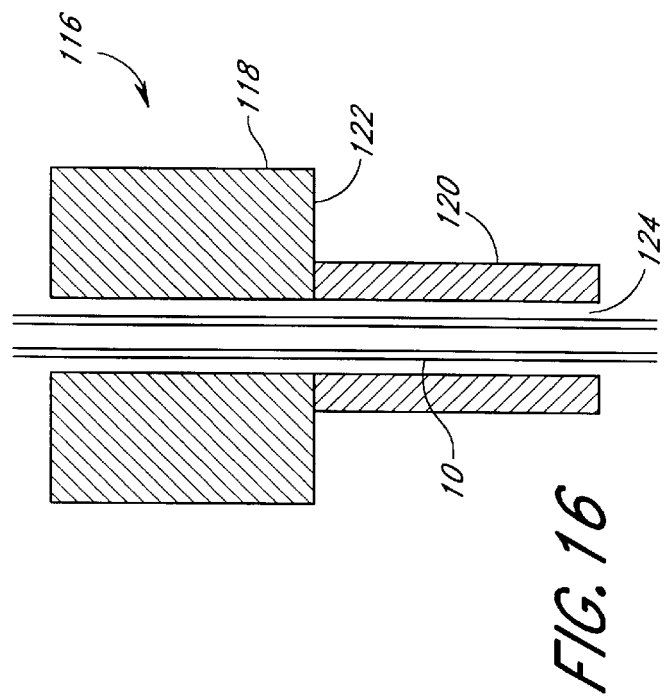
FIG. 16 is a cross section of an adaptor for connecting the capillaries to the upper buffer chamber.

The bundles of capillaries 10 may be connected to the upper buffer chamber 100 via an adapter 116 such as the adaptor illustrated in FIG. 16. The adaptor 116 of FIG. 16 comprises a stopper section 118 and an insertion section 120. The stopper section 118 is wider than the insertion section 120, thereby forming a shoulder 122 at the junction between the stopper section 118 and the insertion section 120. The shoulder 122 prevents the stopper section 118 of the adaptor 116 from being inserted into the upper buffer chamber 100. A channel 124 runs through the stopper section 118 and the insertion section 120. The exterior of the insertion section 120 may be threaded to permit it to be screwed into threads in the apertures 106 in the upper buffer chamber 100, thereby securing the adaptor 116 to the upper buffer chamber 100. A bundle of capillaries 10 passes through the channel 124 in the adaptor 116 such that when the insertion section 120 of the adaptor 116 is inserted into one of the apertures 106 in the upper buffer chamber 100, the ends of the capillaries 10 will contact the buffer solution in the channel 108 in the upper buffer chamber 100. The capillaries 10 may be secured to the adaptor 116 using optical glue or, alternatively, the interior of the adaptor may have grooves or channels therein which secure the capillaries in place.

The embodiments depicted in FIGS. 9 and 10 may include a filling/refilling system for filling or refilling the capillaries 10 and upper buffer chamber 100 with electrophoresis buffer/separation medium without detaching the capillaries 10 from the device. As illustrated in FIGS. 9 and 10, in those embodiments equipped with a filling/refilling system, the upper buffer chamber 100 has at least one inlet port 126 for introducing buffer/separation medium and at least one outlet port 128 for removing buffer/separation medium. In some embodiments, there may be a single port which functions as both an inlet port and an outlet port. Alternatively, the inlet port and the outlet port may be distinct. Furthermore, in some embodiments there may be a plurality of inlet ports and outlet ports. The inlet ports 126 and outlet ports 128 are connected to the apertures 106 in the upper buffer chamber 100 such that the inlet ports 126 and outlet ports 128 are in fluid communication with the channel 108 in the upper buffer chamber 100.

As described in more detail below, when it is desired to fill or refill the capillary tubes 10 and upper buffer chamber 100 with buffer/separation medium, the buffer/separation medium is introduced via the inlet ports 126. Before refilling the capillary tubes 10, the buffer/separation medium used in the previous electrophoresis run may be flushed from the upper buffer chamber 100 and capillary tubes 10 by introducing buffer/separation medium or a rinsing solution through the inlet ports 126 and draining the solution through the outlet ports 128.

In the rotating optical path embodiment of FIG. 10, the inlet ports are in fluid communication with inlet receptacles containing buffer/separation medium via tubing 132 disposed between the inlet receptacles 130 and the inlet ports. The outlet ports 128 are also in fluid communication with outlet receptacles 131 for receiving fluid being drained from the upper buffer chamber 100 via tubing 132 disposed between the outlet receptacles 131 and the outlet ports 128. In the rotating optical path embodiment of FIG. 10, the inlet ports 126 may be connected to the tubing 132 from the inlet receptacles 130 at all times, including during the operation of the device. Alternatively, if desired, the inlet ports 126 may be connected to the tubing 132 from the inlet receptacles 130 only during filling or refilling of the upper buffer chamber 100. Similarly, in this embodiment, the outlet ports 128 may be connected to the tubing from the outlet receptacles 131 at all times, including during the operation of the device. Alternatively, if desired, the outlet ports 128 may be connected to the tubing from the outlet receptacles 131 only during filling/refilling of the upper buffer chamber 100.

In the stationary optical path embodiment of FIG. 9, the inlet ports 126 are not connected to the tubing from the inlet receptacles 130 during the operation of the device. Instead, the inlet ports 126 are connected to the tubing from the inlet receptacles 130 during filling/refilling of the upper buffer chamber 100 while the platform 174 is not rotating. Similarly, in this embodiment, the outlet ports 128 are not connected to the tubing from the outlet receptacles 131 during the operation of the device. Instead, the outlet ports 128 are connected to the tubing from the outlet receptacles 131 during filling/refilling of the upper buffer chamber 100 while the platform 174 is not rotating.

As illustrated in FIGS. 9 and 10, high pressure pumps 134 may be disposed between each inlet port 126 and inlet receptacle 130. Electromagnetic valves 136 are disposed between the inlet ports 126 and the inlet receptacles 130. Electromagnetic valves 136 are also disposed between the outlet ports 128 and the outlet receptacles 131. When the electromagnetic valves 136 are in open position, fluid in the inlet receptacles 130 which are in fluid communication with the inlet ports 126 can be pumped by the high pressure pumps 134 from the inlet receptacles 130 into the channel 108 in the upper buffer chamber 100 and into the capillaries 10. When the electromagnetic valve 136 connected to the outlet port 128 is open, fluid can drain from the outlet port 128 into the outlet receptacle 131 connected to the outlet port 128.

When it is desired to fill the upper buffer chamber 100 and capillaries 10 with fluid, the electromagnetic valves 136 connected to the inlet ports 126 (and/or the inlet ports themselves) are opened and the high pressure pumps 134 are activated. Fluid is pumped from the receptacles 130 connected to the inlet ports 126 into the channel 108 in the upper buffer chamber 100 and into the capillary tubes 10. If it is desired to empty or flush electrophoresis buffer/separation medium already in the channel 108 in the upper buffer chamber 100 and capillaries 10, the electromagnetic valves 136 connected to the inlet ports 126 and the outlet ports 128 (and/or the inlet ports and outlet ports themselves) are opened and fluid is pumped from the receptacles 130 connected to the inlet ports 126, through the inlet ports 126, and out through the outlet ports 128 and the lower ends of the capillary tubes 10. The channel 108 in the upper buffer chamber 100 and the capillary tubes 10 are then refilled with fluid by closing the electromagnetic valve 136 connected to the outlet port 128 (and/or the outlet port itself) while pumping the fluid from the receptacles 130 connected to the inlet ports 126 into the inlet ports 126 until the channel 108 in the upper buffer chamber 100 and the insides of the capillaries 10 have been filled with fluid. If desired, the emptying and refilling of the channel in the upper buffer chamber and the capillary tubes may be under the control of a computer.

As shown in FIGS. 9 and 10, the capillaries 10 extend from the capillary guide 20 into the lower buffer chamber 102 (during electrophoresis of the sample) or into a standard 96 well or 384 well microtiter plate (during loading of the sample). During electrophoresis as well as during sample loading the lower portions of the capillaries 10 pass through a grid 140 having the structure shown in in FIGS. 9, 10, 17, and 18. As best illustrated in the cross section of FIG. 18, the grid 140 comprises a body 188 having a plurality of apertures 144 therein sized for receiving the capillaries 10. For example, the apertures 144 may be 0.5 mm in diameter. The apertures 144 are arranged so as to permit their alignment over the wells 146 of a standard 96 well or 384 well microtiter plate 148. The body may comprise a pair of metallic plates 142 having a spacing section 150 therebetween. The spacing section has apertures 152 therein and is disposed between the metallic plates 142 such that the apertures 152 in the spacing section 150 are aligned with the apertures 144 in the metallic plates 142. Preferably, the spacing section 150 is made of a non-conducting elastic material such as rubber. The metallic plates 142 may be secured to one another using screws 154 located at the corners of the grid 140. The body 188 has a shoulder 190 which contacts the microtiter plate 148 to align the apertures 144 and 152 in the metallic plates and the spacer section with the wells in the microtiter plate 148. As shown in FIG. 18, during loading of the sample the capillaries 10 pass through the apertures 144 in the metallic plates 142 and the apertures 152 in the spacing section 150 such that they contact the sample in the wells 146 of the microtiter plate 148.

Figure 17:
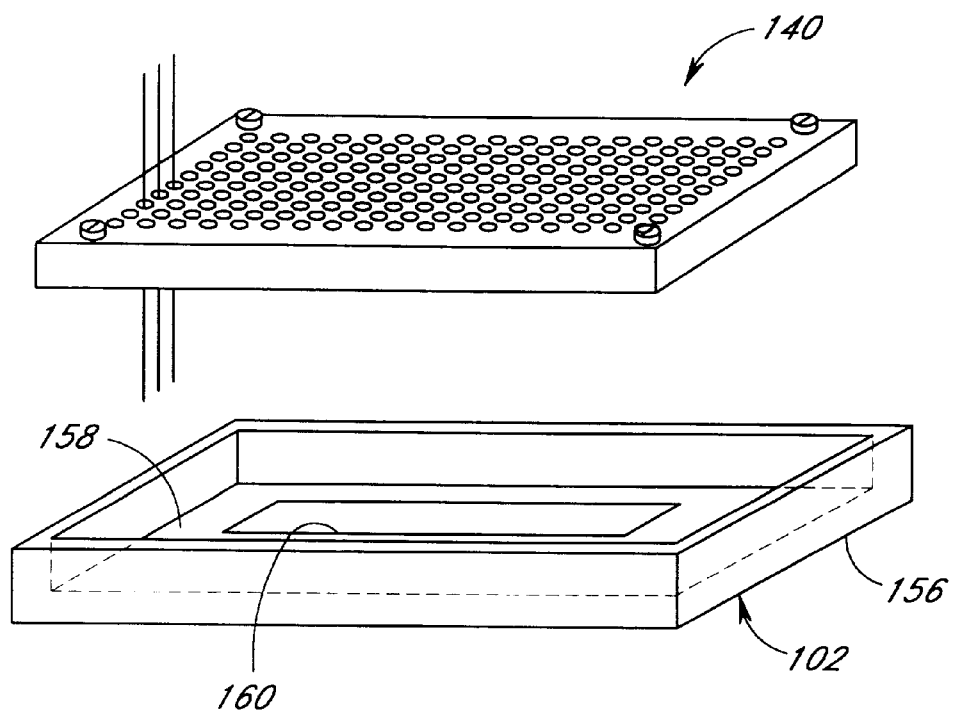
FIG. 17 is a perspective view of the lower buffer chamber and the grid.
Figure 18:
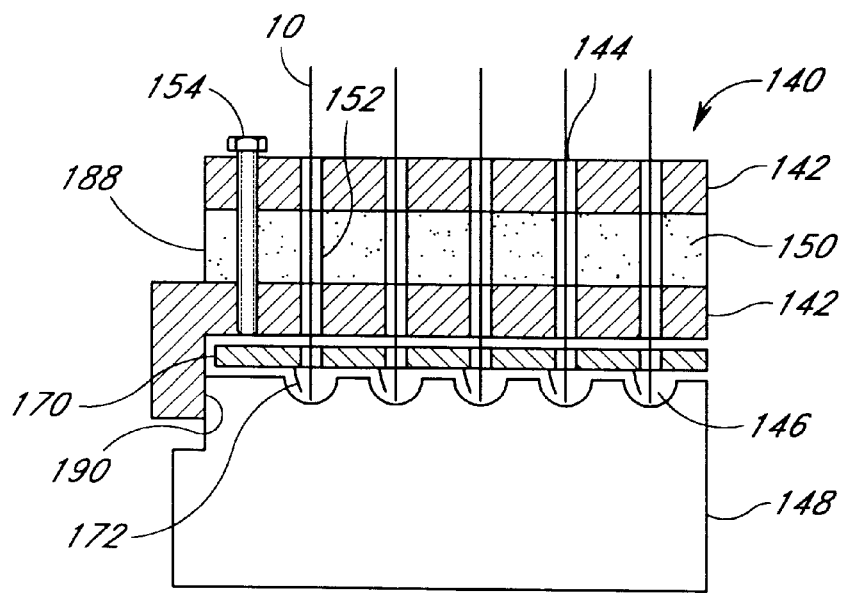
FIG. 18 is a cross section of the grid of FIG. 13 positioned above a microtiter plate.

As shown in FIGS. 9, 10 and 17 during electrophoresis the grid 140 is placed over the lower buffer chamber 102 such that the lower ends of the capillaries contact buffer solution in the lower buffer chamber. The lower buffer chamber 102 may be a rectangular base 156 having a cavity 158 therein for receiving the buffer. A conductor 160 runs along the periphery of the rectangular base 156. The conductor 160 is connected to the voltage source 162. In the stationary optical path embodiment of FIG. 9, the conductor 160 may be connected to the voltage source 162 through a contact (not shown) on the bottom of the lower buffer chamber 102. The contact is electrically connected to the voltage source 162. In the rotating optical path embodiment of FIG. 10, conductor 160 may be connected to the voltage source 162 through a connector (not shown) on the side of the lower buffer chamber 102.

Thus, when the channel 108 in the upper buffer chamber 100 is filled with electrophoresis/separation buffer, a continuous electrical circuit exists between the lower buffer chamber 102 and the upper buffer chamber 100 such that samples loaded in the lower ends of the capillaries 10 can migrate from the lower end of the capillaries to the upper end of the capillaries when a potential difference is applied between the lower buffer chamber 102 and the upper buffer chamber 100.

Use of the present invention for obtaining the sequence of a plurality of DNA samples will now be described.

The channel 108 in the upper buffer chamber 100 and the capillaries 10 are filled with a suitable electrophoresis buffer/separation medium as described above. Preferably, both the electrophoresis buffer and the separation medium comprise a solution of a soluble cellulose derivative. More preferably, the solution of the soluble cellulose derivative which is used both as the electrophoresis buffer and as the separation medium comprises 7M urea, 1X TBE, and 2.7% hydroxypropyl methylcellulose. Alternatively, the separation medium may comprise polyacrylamide gels, such as those described in Swerdlow et al., Anal. Chem. 63:2835–2841, 1991, WO 94/29712, and Huang et al., Anal. Chem. 64:967–972 (1992), the disclosures of which are incorporated herein by reference.

DNA sequencing reactions are performed using conventional techniques such as those described in Huang et al., Anal. Chem. 64:967–992,1992; Quesada et al., Biotechniques 10:616–625, 1991; Swerdlow et al., Anal. Chem. 63:2835–2841, 1991, the disclosures of which are incorporated herein by reference For example, the DNA sequencing techniques used to generate the substrates for sequence determination may comprise the four spectral channel, two spectral channel or one spectral channel techniques described in Swerdlow et al., Anal. Chem. 63:2835–2841, 1991.

Preferably, the four spectral channel technique is used. Briefly, in this technique, four labeling reactions for each DNA sample to be sequenced are performed on a primer which is capable of hybridizing to the DNA in the sample. In each of the four labeling reactions, a different fluorescent label having a different fluorescence pattern is used to label the primer. The fluorescent label may comprise any of the fluorescent labels conventionally employed for DNA sequencing, including FAM, JOE, TAMRA, and ROX.

A separate extension and dideoxynucleotide termination reaction is then performed for each of the four hybridized primers, such that the reaction products for each labeled primer terminate at one of the four nucleotides found in the DNA sequence. The products of the sequencing reactions are desalted and pooled and placed into the sample wells of the 96 or 384 well microtiter plate. Alternatively, if desired, the products of each sequencing reaction may each be placed in separate wells of the microtiter plate.

The grid 140 is secured to the microtiter plate 148 such that the lower ends of the capillary tubes 10 contact the sequencing reaction products in the wells 146. As shown in FIG. 18, a conducting plate 170 may be disposed between the lower metallic plate 142 of the grid 140 and the microtiter plate 148. The conducting plate 170 has short platinum leads 172 thereon which extend into the sample solution in the wells 146. The sequencing reaction products in the wells of the microtiter plate 148 are injected into the capillaries 10 by applying a voltage of 8 kV to the conducting plate for a period of 10–20 seconds.

Alternatively, rather than using the grid 140 and conducting plate 170 during sample loading, a metallic microtiter plate may be used. In this procedure, voltage is applied to the microtiter plate during sample loading.

Following injection of the samples, the grid 140 is placed over the lower buffer chamber 102 containing 1X TBE, 1.2% hydroxypropylmethylcellulose such that the lower ends of the capillaries 10 contact the buffer solution. Electrophoresis is conducted at a voltage of 12 kV for a period of 2 hours. Samples are read as they pass through the detection region of the capillary tubes. In those embodiments in which the electrophoresis system is thermoisolated, the temperature of the electrophoresis may be maintained between 30 degrees Celsius and 80 degrees Celsius. Preferably, the temperature is maintained at 50 degrees Celsius. Temperature regulation may be controlled by a computer 42 connected to a temperature regulator 166.

It will be appreciated that while the above examples describe the use of the present devices for DNA sequencing, the device may also be used in a variety of other applications. For example, the device may be used to sequence macromolecules other than DNA, including polysaccharides.

The present device may also be used to determine whether a subject contains an allelic variation known to confer a particular phenotype, such as a genetic disease. In this application, a DNA sample is obtained from the subject. The DNA is denatured and hybridized to a primer known to hybridize in the region adjacent to the allelic variation known to confer the phenotype of interest. Extension and termination reactions are performed as described above to determine whether the subject carries the allele of interest. Using the present device, DNA samples from a single patient can be analyzed for a plurality of allelic variations. In addition, the present device may be used to analyze DNA samples from numerous subjects to determine whether the subjects carry one or more allelic variations of interest.

The present device may also be used for minisequencing, genotyping, differential gene expression analyses, or fast spectral analysis of biochemical reactions containing fluorophores.

It will be appreciated that no matter how detailed the foregoing appears in text, the invention can be practiced in many ways. As is also stated above, it should further be noted that the use of particular terminology when describing certain features or aspects of the present invention should not be taken to imply that the broadest reasonable meaning of such terminology is not intended, or that the terminology is being re-defined herein to be restricted to including any specific characteristics of the features or aspects of the invention with which that terminology is associated. Thus, although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims and any equivalents thereof. All documents cited herein are incorporated herein by reference in their entirety.

What is claimed is:

1. An electrophoresis apparatus comprising:
    a rotatable array of capillaries, said rotatable array of capillaries comprising a plurality of capillaries wherein each of said plurality of capillaries intersects a plane, and wherein said plurality of capillaries os arranged to intersect said plane such that a curving contour is formed by the intersection points of each of said plurality of capillaries with said plane;
    a capillary guide having an inner surface and an outer surface, wherein said capillary guide includes capillary inputs proximate to a first end and capillary outputs proximate to a second end, and wherein said capillaries are exposed along a portion of said outer surface; and
    a capillary illuminator positioned outside said capillary guide.

2. The electrophoresis apparatus of claim 1, additionally comprising a light collecting lens outside said capillary guide so as to collect light emitted by substances within said capillaries.

3. The electrophoresis apparatus of claim 1, wherein said illuminator comprises one or more lenses for focusing light onto interior portions of said capillaries.

4. The apparatus of claim 1 further comprising a filling/refilling system for filling or refilling said capillaries with fluid.

5. The electrophoresis apparatus of claim 4, wherein said filling/refilling system allows said capillaries to be filled or refilled with fluid without detaching said capillaries from said apparatus.

6. The apparatus of claim 1 further comprising a detector which detects light emitted by substances in said capillaries, wherein the light from said capillary illuminator and the light detected by said detector are not coaxial along any portion of their paths.

7. A method of sequencing a plurality of strands of nucleic acid comprising the steps of:
    generating a set of nucleic acid fragments labeled with one or more dyes wherein the fragments in each member of said set specifically terminate at one of the four nucleotides which occur in DNA;
    introducing one or more members of said set of labeled nucleic acids into one or more of a plurality of capillary tubes arranged in an array in an electrophoresis apparatus comprising a filling/refilling system for filling or refilling said capillaries with fluid, wherein each of said plurality of capillaries intersects a plane, and wherein said plurality of capillaries is arranged to intersect said plane such that a curving contour is formed by the intersection points of each of said plurality of capillaries with said plane;
    separating said labeled fragments by size;
    illuminating said fragments; and
    detecting light emitted by said one or more dyes when a signal generated by light scattered from said capillaries is maximal.

8. The method of claim 7, wherein the step of detecting light comprises the step of routing said light to a single line charge coupled device.

9. The method of claim 7, wherein said step of illuminating said fragments comprises the step of sweeping a light beam around the interior of said array.

10. The method of claim 7, wherein said step of illuminating said fragments comprises the step of sweeping the exterior of said array past a light beam.

11. The method of claim 7, wherein said introducing step comprises introducing one or more members of said set of labeled nucleic acids into one or more of a plurality of capillary tubes arranged in an array in an electrophoresis apparatus comprising a filling/refilling system for filling or refilling said capillaries with fluid without detaching said capillaries from said apparatus, wherein each of said plurality of capillaries intersects a plane, and wherein said plurality of capillaries is arranged to intersect said plane such that a curving contour is formed by the intersection points of each of said plurality of capillaries with said plane.

12. A method of making a capillary electrophoresis apparatus comprising the steps of:
    arranging a plurality of capillaries such that each of said plurality of capillaries intersects a plane, and wherein said plurality of capillaries is arranged to intersect said plane such that a curving contour is formed by the intersection points of each of said plurality of capillaries with said plane;
    mounting a light collecting lens adjacent to at least one of said plurality of capillaries;
    mounting a synchronization detector in a location in which said synchronization detector receives at least a portion of the light received by said light collecting lens wherein said synchronization detector generates a signal having a magnitude indicative of the magnitude of the light received by said light collecting lens; and
    connecting a filling/refilling system to said capillaries such that said capillaries can be filled or refilled with fluid.

13. The method of claim 12, wherein said step of arranging comprises the steps of mounting said plurality of capillaries to a capillary guide and mounting said capillary guide to a rotatable platform.

14. The method of claim 12, wherein said step of mounting a light collecting lens comprises mounting a light collecting lens onto a rotatable platform.

15. The method of claim 12, wherein said connecting step comprises connecting a filling/refilling system to said capillaries such that said capillaries can be filled or refilled with fluid without detaching said capillaries from said apparatus.

16. An electrophoresis apparatus comprising:
    a capillary array comprising a plurality of capillaries, said capillaries having sample input ends and sample output ends, wherein each of said plurality of capillaries intersects a plane, and wherein said plurality of capillaries is arranged to intersect said plane such that a curving contour is formed by the intersection points of each of said plurality of capillaries with said plane;
    a light source configured to direct light onto said capillary array;
    an illuminator mounted on a rotatable platform within said capillary array, wherein said illuminator is configured to focus light from said light source onto individual ones of said capillaries, and wherein said illuminator is further configured to direct light emitted by substances within individual ones of said capillaries out of said capillary array;
    a synchronization detector positioned to collect at least a portion of the light scattered by said capillaries, wherein said synchronization detector generates a signal having a magnitude indicative of the alignment of said illuminator with said capillaries and indicative of the extent to which said light from said light source is focussed on said capillaries;

a spectral separator configured to receive said light emitted by said substances within said capillaries, and to emit said light after spectral separation; and at least one single line charge coupled device positioned to receive light of a first wavelength emitted by said spectral separator at a first location thereon, and to receive light of a second wavelength emitted by said spectral separator at a second location thereon.

17. The electrophoresis apparatus of claim 16, additionally comprising a capillary guide having inner and outer surfaces and first and second ends, wherein said capillary guide includes capillary inputs on one end and capillary outputs on another end, and wherein said capillaries are exposed along at least a portion of said inner surface of said capillary guide.

18. An apparatus comprising:

a capillary array comprising plurality of capillaries, said capillaries having sample input ends and sample output ends, wherein each of said plurality of capillaries intersects a plane, and wherein said plurality of capillaries is arranged to intersect said plane such that a curving contour is formed by the intersection points of each of said plurality of capillaries with said plane, a light source configured to direct light onto said capillary array;

an illuminator mounted on a rotatable platform within said capillary array, wherein said illuminator is configured to focus light from said light source onto individual ones of said capillaries, and wherein said illuminator is further configured to direct light emitted by substances within individual ones of said capillaries out of said capillary array;

a spectral separator configured to receive said light emitted by said substances within said capillaries, and to emit said light after spectral separation;

at least one single line charge coupled device positioned to receive light of a first wavelength emitted by said spectral separator at a first location thereon and to receive light of a second wavelength emitted by said spectral separator at a second location thereon;

a capillary guide having inner and outer surfaces and first and second ends wherein said capillary guide includes capillary inputs on one end and capillary outputs on another end, and wherein said capillaries are exposed along at least a portion of said inner surface of said capillary guide; and an upper buffer chamber substantially surrounding one end of said capillary guide, said upper buffer chamber comprising a housing having a channel running along its periphery and one or more apertures therein for receiving said output ends of said capillaries such that said output ends can contact buffer in said channel, an electrical conductor running along said channel, and a connector electrically connected to said conductor for applying a voltage to said sample output ends of said capillaries.

19. The apparatus of claim 18 further comprising a filling/refilling system for filling or refilling said capillaries with fluid.

20. The electrophoresis apparatus of claim 19, wherein said filling/refilling system allows said capillaries to be filled or refilled with fluid without detaching said capillaries from said apparatus.

21. The apparatus of claim 19 wherein said filling/refilling system comprises one or more inlet ports in fluid communication with said capillaries and said channel for supplying fluid to said capillaries.

22. The apparatus of claim 21 wherein said filling/refilling system further comprises one or more outlet ports in fluid communication with said channel in said upper buffer chamber for removing fluid from said channel in said upper buffer chamber.

23. The apparatus of claim 22 wherein said filling/refilling system further comprises electromagnetic valves connected to said inlet ports and said outlet ports for regulating fluid flow through said inlet and outlet ports.

24. The apparatus of claim 23 wherein said filling/refilling system further comprises one or more receptacles containing said fluid, said receptacles being in fluid communication with said capillaries and said channel, and a pump for transferring said fluid from said receptacles to said capillaries and said channel.

25. The apparatus of claim 24 wherein said pump comprises a high pressure pump.

26. The apparatus of claim 24 further comprising a lower buffer chamber positioned such that said sample input ends of said capillaries can contact buffer in said lower buffer chamber.

27. An electrophoresis apparatus comprising:

a rotatable array of capillaries, said capillaries having sample input ends and sample output ends wherein each of said plurality of capillaries intersects a plane, and wherein said plurality of capillaries is arranged to intersect said plane such that a curving contour is formed by the intersection points of each of said plurality of capillaries with said plane;

a light source configured to direct light onto said array;

a spectral separator configured to receive said light emitted by substances within said capillaries, and to emit said light after spectral separation;

at least one single line charge coupled device positioned to receive light of a first wavelength emitted by said spectral separator at a second location thereon; and a capillary guide having inner and outer surfaces and first and second ends, wherein said capillary guide includes capillary inputs on one end and capillary outputs on another end, and wherein said capillaries are exposed along at least a portion of said outer surface of said capillary guide.

28. The apparatus of claim 27, further comprising a synchronization detector which receives light scattered by said capillaries and generates a signal having a magnitude indicative of the amount of light scattered by said capillaries.

29. The apparatus of claim 27, wherein said light from said light source and said light received by said spectral separator are not coaxial along any portion of their paths.

30. An electrophoresis apparatus comprising:

a plurality of capillaries having sample input ends and sample output ends;

a light source;

a rotatable illuminator configured to direct light from said light source onto said capillaries;

a detector configured to detect light emitted by substances within said plurality of capillaries;

a synchronization detector which receives light scattered by said capillaries and generates a signal having a magnitude indicative of the amount of light scattered by said capillaries; and a filling/refilling system for filling or refilling said capillaries with fluid.

31. The apparatus of claim 30, wherein said filling/refilling system allows said capillaries to be filled or refilled with fluid without detaching said capillaries from said apparatus.

32. The apparatus of claim 30, further comprising a capillary guide having an inner surface and an outer surface, wherein said capillary guide includes capillary inputs proximate to a first end and capillary outputs proximate to a second end, and wherein said capillaries are exposed along a portion of said inner surface.

33. The electrophoresis apparatus of claim 32, wherein said illuminator is positioned inside said capillary guide.

34. The electrophoresis apparatus of claim 33, additionally comprising a light collecting lens inside said capillary guide so as to collect light emitted by substances within said capillaries.

35. The electrophoresis apparatus of claim 33, wherein said illuminator comprises one or more lenses for focusing light onto interior portions of said capillaries.

36. The electrophoresis apparatus of claim 33, wherein said capillary illuminator is mounted on a rotatable platform so as to sequentially illuminate each of said plurality of capillaries.

37. The electrophoresis apparatus of claim 30, wherein said filling/refilling system allows said capillaries to be filled or refilled with fluid without detaching said capillaries from said apparatus.

38. An electrophoresis apparatus comprising:

a rotatable plurality of capillaries having sample input ends and sample output ends;

a light source;

an illuminator configured to direct light from said light source onto said capillaries;

a detector configured to detect light emitted by substances within said plurality of capillaries; and a synchronization detector which receives light scattered by said capillaries and generates a signal having a magnitude indicative of the amount of light scattered by said capillaries.

39. The apparatus of claim 38 further comprising a filling/refilling system for filling or refilling said capillaries with fluid.

40. The electrophoresis apparatus of claim 39, wherein said filling/refilling system allows said capillaries to be filled or refilled with fluid without detaching said capillaries from said apparatus.

41. The apparatus of claim 38, wherein said light from said light source and said light detected by said detector are not coaxial along any portion of their paths.

42. A method of performing electrophoresis comprising the steps of:

rotating an array of capillaries;

illuminating capillaries in said rotating array; and detecting light emitted by substances in said capillaries, wherein said detecting step is performed when the magnitude of a signal from a synchronization detector indicates that the amount of light being scattered by said capillaries is maximal.

43. The method of claim 42, wherein said step of rotating comprises rotating an array of capillaries, wherein each of said capillaries intersects a plane, and wherein said capillaries are arranged to intersect said plane such that a curving contour is formed by the intersection points of each of said capillaries with said plane.

44. The method of claim 42, wherein the light in said illuminating step and the light in said detecting step are not coaxial along any portion of their paths.

45. A method of performing electrophoresis comprising the steps of:

rotating an illuminator past an array of capillaries in an apparatus;

detecting light emitted by substances in said capillaries when the magnitude of a signal from a synchronization detector indicates that the amount of light scattered by said capillaries is maximal; and filling/refilling said capillaries with fluid using a filling/refilling system on said apparatus.

46. The method of claim 45, wherein said step of rotating an illuminator past an array of capillaries comprises rotating an illuminator past an array of capillaries, wherein each of said capillaries intersects a plane, and wherein said capillaries are arranged to intersect said plane such that a curving contour is formed by the intersection points of each of said capillaries with said plane.

47. The method of claim 45, wherein said filling/refilling step comprises filling/refilling said capillaries with fluid using a filling/refilling system on said apparatus without detaching said capillaries from said apparatus.

48. An apparatus comprising:

a plurality of capillaries, said capillaries having sample input ends and sample output ends, wherein each of said plurality of capillaries intersects a plane, and wherein said plurality of capillaries is arranged to intersect said plane such that a curving contour is formed by the intersection points of each of said plurality of capillaries with said plane;

a capillary guide having an inner surface and an outer surface, wherein said capillary guide includes capillary inputs proximate to a first end and capillary outputs proximate to a second end, and wherein said capillaries are exposed along a portion of said outer surface;

a capillary illuminator positioned outside said capillary guide;

a filling/refilling system for filling or refilling said capillaries with fluid; and an upper buffer chamber, said upper buffer chamber comprising a housing having a channel running along its periphery and one or more apertures therein for receiving said output ends of said capillaries such that said output ends can contact buffer in said channel, an electrical conductor running along said channel, and a connector electrically connected to said conductor for applying a voltage to said sample output ends of said capillaries.

49. The apparatus of claim 48, wherein said filling/refilling system comprises one or more inlet ports in fluid communication with said capillaries and said channel for supplying fluid to said capillaries.

50. The apparatus of claim 49 wherein said filling/refilling system further comprises one or more outlet ports in fluid communication with said channel in said upper buffer chamber for removing fluid from said channel in said upper buffer chamber.

51. The apparatus of claim 50, wherein said filling/refilling system further comprises electromagnetic valves connected to said inlet ports and said outlet ports for regulating fluid flow through said inlet and outlet ports.

52. The apparatus of claim 51, wherein said filling/refilling system further comprises one or more receptacles containing said fluid, said receptacles being in fluid communication with said capillaries and said channel, and a pump for transferring said fluid from said receptacles to said capillaries and said channel.

53. The apparatus of claim 52, wherein said pump comprises a high pressure pump.

54. The apparatus of claim 52, further comprising a lower buffer chamber positioned such that said capillaries can contact buffer in said lower buffer chamber.

55. A method of sequencing a plurality of strands of nucleic acid comprising the steps of:

generating a set of nucleic acid fragments labeled with one or more dyes wherein the fragments in each member of said set specifically terminate at one of the four nucleotides which occur in DNA;

introducing one or more members of said set of labeled nucleic acids into one or more of a plurality of capillary tubes in an electrophoresis apparatus comprising a plurality of capillaries wherein each of said plurality of capillaries intersects a plane and has an interior and an exterior surface, and wherein said plurality of capillaries is arranged to intersect said plane such that a curving contour is formed by the intersection points of each of said plurality of capillaries with said plane and a capillary guide having an inner surface and an outer surface, wherein said capillary guide includes capillary inputs proximate to a first end and capillary outputs proximate to a second end, and wherein the exterior surface of said capillaries are exposed along a portion of said outer surface;

separating said labeled fragments by size;

illuminating said fragments by rotating said capillary guide such that the exterior surfaces of said plurality of capillary tubes are sequentially illuminated by a light beam; and detecting light emitted by said one or more dyes.

56. The method of claim 55, wherein the step of detecting light comprises the step of routing said light to a single line charge coupled device.

57. The method of claim 55 further comprising illuminating said capillaries with light traveling along a first axis and detecting light which is emitted by said substances along a second axis, said first axis and said second axis not being coaxial along any portion of their paths.

58. An apparatus comprising:

a capillary array comprising plurality of capillaries, said capillaries having sample input ends and sample output ends, wherein each of said plurality of capillaries intersects a plane, and wherein said plurality of capillaries is arranged to intersect said plane such that a curving contour is formed by the intersection points of each of said plurality of capillaries with said plane;

a light source configured to direct light onto said capillary array;

an illuminator mounted on a rotatable platform within said capillary array, wherein said illuminator is configured to focus light from said light source onto individual ones of said capillaries, and wherein said illuminator is further configured to direct light emitted by substances within individual ones of said capillaries out of said capillary array; and an upper buffer chamber comprising a housing having a channel running along its periphery and one or more apertures therein for receiving said output ends of said capillaries such that said output ends can contact buffer in said channel, an electrical conductor running along said channel, and a connector electrically connected to said conductor for applying a voltage to said sample output ends of said capillaries.

59. An apparatus comprising:

a rotatable array of capillaries, said rotatable array of capillaries comprising a plurality of capillaries wherein each of said plurality of capillaries intersects a plane, and wherein said plurality of capillaries is arranged to intersect said plane such that a curving contour is formed by the intersection points of each of said plurality of capillaries with said plane;

a stationary capillary illuminator positioned to sequentially illuminate each of said plurality of capillaries in said rotatable array of capillaries; and an upper buffer chamber comprising a housing having a channel running along its periphery and one or more apertures therein for receiving said output ends of said capillaries such that said output ends can contact buffer in said channel, an electrical conductor running along said channel, and a connector electrically connected to said conductor for applying a voltage to said sample output ends of said capillaries.

* * * * *

UNITED STATES PATENT AND TRADEMARK OFFICE
CERTIFICATE OF CORRECTION

PATENT NO.    : 6,103,083
DATED         : August 15, 2000
INVENTOR(S)   : Irena N. Merenkova and Maxim Brevnov It is certified that error appears in the above-identified patent and that said Letters Patent is hereby corrected as shown below:

<u>Column 15,</u>
Line 13, "os", should read -- is --.

Signed and Sealed this

Third Day of September, 2002

Attest:

Attesting Officer

JAMES E. ROGAN
*Director of the United States Patent and Trademark Office*